US007555435B2

(12) United States Patent
Ball et al.

(10) Patent No.: US 7,555,435 B2
(45) Date of Patent: Jun. 30, 2009

(54) SYSTEMS AND METHODS FOR LOOK-ALIKE SOUND-ALIKE MEDICATION ERROR MESSAGING

(75) Inventors: Sarah Johnston Ball, Charleston, SC (US); Suzanne Agner Coffman, Charleston, SC (US); Roger George Pinsonneault, Alpharetta, GA (US)

(73) Assignee: NDCHealth Corporation, Atlanta, GA (US)

( * ) Notice: Subject to any disclaimer, the term of this patent is extended or adjusted under 35 U.S.C. 154(b) by 1101 days.

(21) Appl. No.: 10/339,000

(22) Filed: Jan. 9, 2003

(65) Prior Publication Data

US 2004/0059600 A1 Mar. 25, 2004

Related U.S. Application Data

(60) Provisional application No. 60/413,563, filed on Sep. 25, 2002.

(51) Int. Cl.
*G06Q 50/00* (2006.01)
*G06Q 40/00* (2006.01)

(52) U.S. Cl. ............................................ 705/2; 705/4

(58) Field of Classification Search ...................... 705/2
See application file for complete search history.

(56) References Cited

U.S. PATENT DOCUMENTS 4,547,851 A 10/1985 Kurland
5,048,870 A 9/1991 Mangini et al.
5,737,539 A * 4/1998 Edelson et al. ................. 705/3
5,740,268 A 4/1998 Nishikawa et al.
5,845,255 A 12/1998 Mayaud
5,950,630 A * 9/1999 Portwood et al. ........... 128/897
5,958,930 A 9/1999 Gangjee
6,272,472 B1 8/2001 Danneels et al.
6,529,892 B1 * 3/2003 Lambert ...................... 706/55
6,978,286 B2 * 12/2005 Francis et al. ............... 708/132
7,490,047 B2 2/2009 Brown et al.
2001/0056358 A1 * 12/2001 Dulong et al. ................. 705/2
2002/0042725 A1 4/2002 Mayaud (Continued)

OTHER PUBLICATIONS

PR Newswire, "NDCHealth Announces NDC Rx Safety Advisor to Help Prevent Look-Alike Sound-Alike Dispensation Errors", New York: Aug. 12, 2002. p. 1.*

(Continued)

*Primary Examiner*—C. Luke Gilligan
*Assistant Examiner*—Robert Sorey
(74) *Attorney, Agent, or Firm*—Sutherland Asbill & Brennan LLP

(57) ABSTRACT

Systems and methods are provided for look-alike sound-alike medication error messaging. Prescription data relating to a prescription is parsed to identify a submitted drug product and a submitted daily dosage. An absolute dose screening process may be executed to determine whether the submitted daily dosage meets absolute dosing criteria for the submitted drug product. A typical dose screening process may be executed to determine whether the submitted daily dosage meets statistically derived typical dosing criteria for the submitted drug product and any look-alike sound-alike alternative drug products. In addition, one or more likelihood indicators may be assigned to the submitted drug product in relation to associated look-alike sound-alike drug pairs. If it is determined that the prescription should be rejected based on typical dosing criteria, absolute dosing criteria, or the likelihood indicator(s), a reject message may be built for presentation to the pharmacist.

32 Claims, 6 Drawing Sheets

U.S. PATENT DOCUMENTS

2002/0087554 A1* 7/2002 Seelinger ..................... 707/10
2004/0019464 A1* 1/2004 Martucci et al. ............ 702/189
2004/0172281 A1* 9/2004 Stanners ........................ 705/2
2004/0188998 A1* 9/2004 Henthorn .................... 283/900

OTHER PUBLICATIONS

Office Action dated Jun. 21, 2005, in U.S. Appl. No. 10/339,108.
Response to Election /Restriction dated Jul. 25, 2005, in U.S. Appl. No. 10/339,108.
Office Action dated Sep. 16, 2005, in U.S. Appl. No. 10/339,108.
Dec. 20, 2005 Amendment and Response to Non-Final Office Action in U.S. Appl. No. 10/339,108.
Final Office Action dated Mar. 16, 2006, in U.S. Appl. No. 10/339,108.
Jun. 19, 2006 Response to Final Office Action in U.S. Appl. No. 10/339,108.
Final Office Action dated Sep. 7, 2006, in U.S. Appl. No. 10/339,108.
Jan. 8, 2007 Amendment and Response to Final Office Action in U.S. Appl. No. 10/339,108.
Office Action dated Mar. 5, 2007, in U.S. Appl. No. 10/339,108.
Jun. 5, 2007 Amendment and Response to Office Action in U.S. Appl. No. 10/339,108.
Office Action dated Apr. 2, 2007 in U.S. Appl. No. 10/339,612.
Amendment and Response to Office Action dated Jul. 2, 2007 in U.S. Appl. No. 10/339,612.
Office Action dated Apr. 19, 2007 in U.S. Appl. No. 10/339,230.
Amendment and Response to Office Action dated Jul. 19, 2007 in U.S. Appl. No. 10/339,230.
Untitled Webpage, "Apparatus, Method and Product for Multi-attribute Drug Comparison to Avoid Medical Errors" University of Illinois at Chicago, pp. 1-2, available at www.uic.edu.
1998 Conference Archive, "Enhancing Patient Safety and Reducing Errors to Health Care", pp. 1-9, available at www.npsf.org.
A Publication of the USP Practitioner's Reporting Network, "USP Quality Review", U.S. Pharmacopeia, No. 66, May 1999.
Webpage entitled: Institute for Safe Medication Practices, "Prescription mapping can improve efficiency while minimizing errors with look-alike products", available at www.ismp.org.
Webpage entitled: ISMP Quarterly Action Agenda: Oct.-Dec. 2001, Jan. 23, 2002; pp. 1-3, available at www.ismp.org.
Final Office Action dated Sep. 20, 2007 in U.S. Appl. No. 10/339,612.
Final Office Action dated Aug. 23, 2007 in U.S. Appl. No. 10/339,108.
Final Office Action dated Oct. 18, 2007 in U.S. Appl. No. 10/339,230.
Jan. 18, 2008 Amendment and Response to Final Office Action in U.S. Appl. No. 10/339,230.
Office Action dated Feb. 28, 2008 in U.S. Appl. No. 10/339,230.
Jun. 30, 2008 Amendment and Response to Non-Final Office Action in U.S. Appl. No. 10/339,230.
Dec. 20, 2007 Amendment and Response to Final Office Action in U.S. Appl. No. 10/339,612.
Office Action dated Jan. 25, 2008 in U.S. Appl. No. 10/339,612.
Apr. 25, 2008 Amendment after Non-Final rejection in U.S. Appl. No. 10/339,612.
Final Office Action dated Aug. 6, 2008 in U.S. Appl. No. 10/339,612.
Jan. 23, 2008 Amendment and Response to Final Office Action in U.S. Appl. No. 10/339,108.
Notice of Informal or Non-Responsive Amendment dated Apr. 15, 2008 in U.S. Appl. No. 10/339,108.
Final Office Action mailed Sep. 29, 2008 for U.S. Appl. No. 10/339,230.
Amendment and Response to Final Office Action for U.S. Appl. No. 10/339,230 filed Jan. 29, 2009.
Notice of Abandonment for Failure to Respond to Office Action for U.S. Appl. No. 10/339,108 mailed Nov. 4, 2008.
Non-Final Office Action mailed Mar. 27, 2009 for U.S. Appl. No. 10/339,230.

* cited by examiner

SYSTEMS AND METHODS FOR LOOK-ALIKE SOUND-ALIKE MEDICATION ERROR MESSAGING

RELATED APPLICATIONS

The present application claims the benefit of U.S. Provisional Patent Application Ser. No. 60/413,563 filed Sep. 25, 2002, which is hereby incorporated by reference as if set forth fully herein.

TECHNICAL FIELD

The present invention relates generally to medication errors involving medication names that look and/or sound alike. More particularly, the present invention relates to systems and methods for intelligently detecting look-alike sound-alike medication errors within prescription transactions and the like.

BACKGROUND OF THE INVENTION

Medication errors are increasingly recognized as an important cause of preventable deaths and injuries. A significant percentage of medication errors occur when a prescribed medication is confused with a non-prescribed medication and the non-prescribed medication is dispensed to the patient. Medication brand names can look like other brand names when handwritten or may be mistaken for another drug when ordered orally. Generic medication names can resemble other generic medication names or even brand names. Medication errors can also occur when the labeling or packaging of multiple drugs is too similar. Medication errors resulting from such confusion between drugs are often referred to as look-alike sound-alike ("LASA") medication errors.

Millions of dollars may be spent establishing a brand name well before a drug is ever introduced to the market. Thus, drug manufacturers are extremely reluctant to change medication brand names. Changing a generic drug name can also be a complicated and expensive undertaking. Such a modification would affect all the companies that manufacture the compound, not to mention the numerous text references and software programs that refer to the generic drug name. Generic drug names may be based on word stems related to particular drug class, a factor that causes much overlap between generic drug names.

Given the resistance to change a medication name, efforts have been made to anticipate and avoid LASA medication errors before a medication name is adopted. As one example, special software has been developed to screen proposed medication names against databases of existing medication names. The software computes a numerical similarity score between the proposed drug name and other drug names. The proposed drug name is measured for its resemblance to all of the drug names stored in a massive database of medication brand and generic names.

Even with pre-screening techniques, LASA errors continue to occur. Short of a medication name change, alert systems are used to alert pharmacists of potential LASA errors. Such systems generate a warning message any time a drug product having a drug name that is included in a LASA drug pair is detected in a prescription transaction. The term "LASA drug pair," as used herein, refers to two or more drug names that are known to be confused with each other. Each member of a LASA drug pair can be referred to as a LASA alternative drug name to the other member(s). Systems that generate warning messages any time a drug product having a drug name that is included in a LASA drug pair is detected can generate a high volume of messages, the majority of which are "false positives." As a result, such warning messages tend to be more of a burden to busy pharmacists than an aide.

It is clear that existing pharmacy decision support and practice management systems do not adequately protect against LASA medication errors. What is needed is a system and method for intelligently detecting LASA medication errors based on more than simply whether a drug name is included in a LASA drug pair. The sensitivity of such a system and method should be adjustable, so as to provide the ability to increase or decrease the rate of LASA medication error messaging. There is further a need for a system and method that monitors prescription transactions for possible LASA medication errors and generates messages when there is a likelihood that a different medication, dispense quantity, or days supply is more appropriate.

SUMMARY OF THE INVENTION

The present invention provides systems and methods for look-alike sound-alike medication error messaging. A submitted drug product and a submitted daily dosage for a prescription are identified from prescription data, such as that which is included in a prescription transaction or the like. If the submitted drug product is associated with at least one look-alike sound-alike drug pair comprising at least one look-alike sound-alike alternative drug name, determinations may be made as to whether the submitted daily dosage meets pre-determined statistically derived typical dosing criteria and/or absolute dosing criteria. In addition, a likelihood indicator may be determined for the submitted drug product. Likelihood indicators may be used to quantify the relative probability of whether a drug product is involved in a LASA medication error.

Determining whether the submitted daily dosage meets pre-determined typical dosing criteria may involve determining whether the submitted daily dosage is typical or atypical for the submitted drug product and/or for any LASA alternative drug products associated with any LASA alternative drug name. If the submitted daily dosage does not meet the statistically derived typical dosing criteria for the submitted drug product, a typical dose message may be determined for the prescription. The statistically derived typical dosing criteria may optionally be specific to patient demographic group, treatment type, illness type or physician specialty. A clinical significance may also be determined for the look-alike sound-alike drug pair. Clinical significance may be a value used to quantify the consequences of a look-alike sound-alike medication error involving the look-alike sound-alike drug pair. A typical dose edit action may be determined based on the clinical significance of the look-alike sound-alike drug pair. The typical dose edit action may further be determined based on whether the prescription relates to a new prescription or a refill. The typical dose edit action may be used to indicate whether the prescription should be rejected.

Determining whether the submitted daily dosage meets pre-determined absolute dosing criteria may involve determining whether the submitted daily dosage exceeds an absolute maximum daily dosage or is less than an absolute minimum daily dosage for the submitted drug product. If the submitted daily dosage does not meet the absolute dosing criteria for the submitted drug product, an absolute dose message may be determined for the prescription. The absolute dose edit action may also be determined based on whether the prescription relates to a new prescription or a refill. The absolute dose edit action may be used to indicate whether the prescription should be rejected. Absolute dosing criteria may optionally be specific to patient demographic group, treatment type and illness type.

Likelihood indicators may be stored in a database and may be pre-determined based on factors such as a degree of similarity between look-alike sound alike drug names, prescribing frequencies assigned to the drug product associated with the look-alike sound-alike drug pair, and the availability of associated drug products in same, look-alike or sound-alike strengths, as well as other likelihood enhancing or diminishing factors. Degree of similarity may be computed as the Levenshtein Distance between the drug names of the submitted drug product and the look-alike sound-alike alternative drug product. Prescribing frequencies may be categorized as being either high, medium or low. Low-low, high-low or low-high combinations of prescribing frequencies for the submitted drug product and the look-alike sound-alike alternative drug product may be considered to have the potential for confirmation bias. A likelihood edit action may be determined based on the likelihood indicator and whether the prescription relates to a new or refill prescription. The likelihood edit action may be used to indicate whether the prescription should be rejected. A likelihood message may be determined based on the likelihood edit action.

If at least one of the typical dose edit action, the absolute dose edit action and the likelihood edit action indicates that the prescription should be rejected, a reject message may be built and presented to the pharmacist. The reject message may include the absolute dose message if the absolute dose edit action indicates that the prescription should be rejected, the typical dose message if the typical dose edit action indicates that the prescription should be rejected, and the likelihood message if the likelihood edit action indicates that the prescription should be rejected. Inclusion of more than one of the absolute dose message, the typical dose message and the likelihood message in the reject message is dependent on there being sufficient text space in the reject message, with first preference given to the absolute dose message and second preference given to the typical dose message.

These and other features, aspect and embodiments of the invention will be described in more detail below.

DETAILED DESCRIPTION OF THE INVENTION

Figure 1:
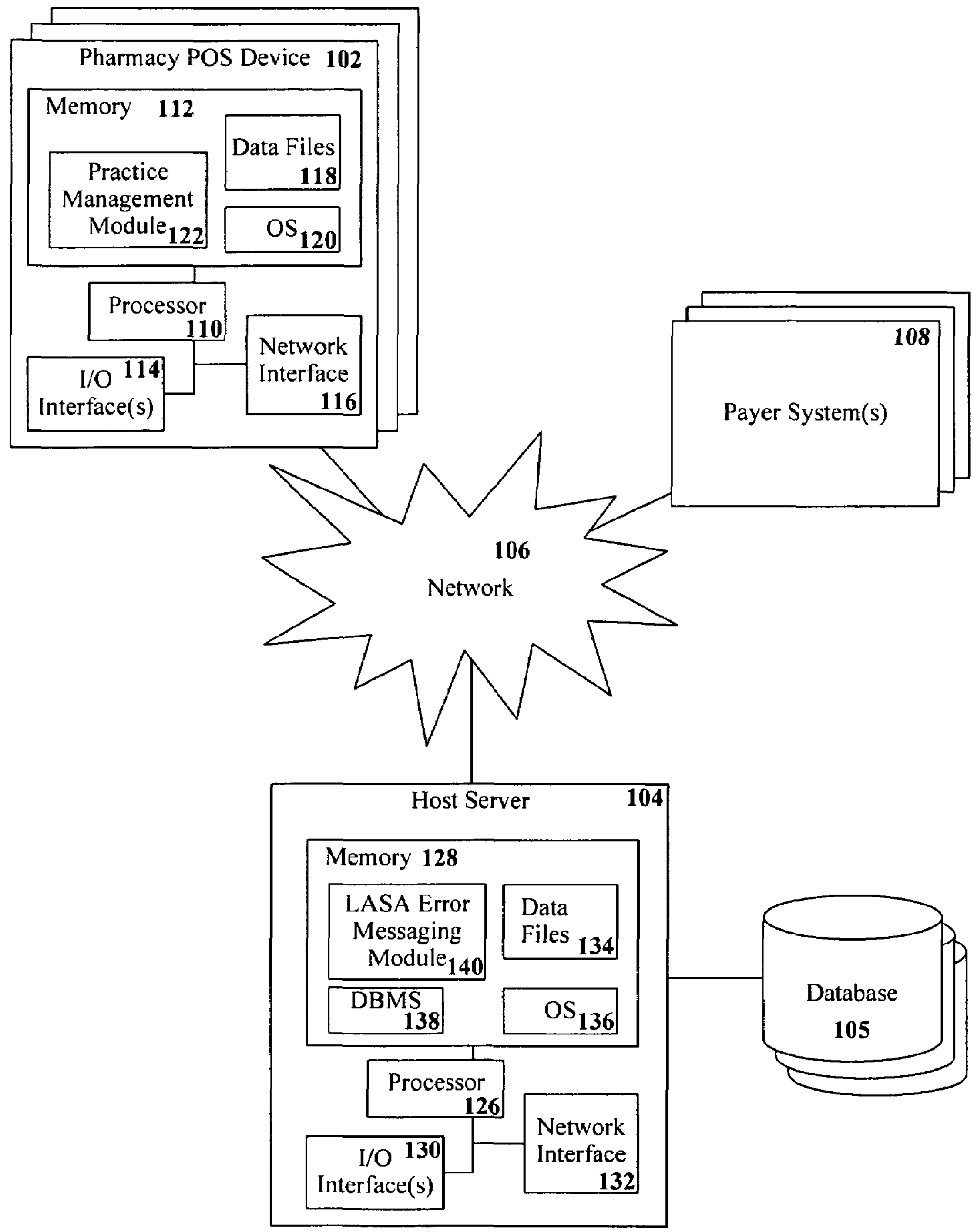
FIG. 1 is a block diagram illustrating an exemplary system in accordance with certain exemplary embodiments of the present invention.

The present invention provides systems and methods for look-alike sound-alike ("LASA") medication error messaging. The systems and methods of the present invention monitor prescription transactions and return appropriate messages to pharmacists or other health care providers when the characteristics of a prescription transaction indicate the possibility that a different medication, different dispense quantity or different daily supply is more appropriate. One or more screening processes are used to screen prescription transactions for possible medication errors. The invention provides flexibility for activating and deactivating certain screening processes, the choice of which and the sensitivity of included parameter settings will determine how many LASA medication error messages are returned to the pharmacist or other health care provider and the content of those messages.

The terms "medication" and "drug" are used synonymously herein. The terms "medication name" and "drug name" may be used herein to refer generally to either a brand name or a generic name of a medication. A "drug product" is the specific item dispensed to the patient and is identified by the ingredient(s)/strength(s)/dosage form combination dispensed to patient. Drug products are commonly identified by a unique identifier, examples of which include, but are not limited to, Generic Code Number sequence numbers ("GCN*SEQNO") and Generic Product Identifiers ("GPI").

A National Drug Code number ("NDC#"), identifies the labeler/vendor, product, and trade package size. Thus, although multiple drug products may share a common ingredient(s)/strength(s)/dosage form combination, each drug product having a different brand, package size or labeler/vendor is identified by a unique NDC#. In certain embodiments of the present invention, drug products are identified by NDC# in prescription claim transactions. In other embodiments, such as those involving electronic prescriptions or other types of prescription transactions, more generic product identifiers may be used.

As mentioned previously, a "LASA drug pair" is defined herein as two or more drug names that are known to be confused with each other. Each drug name in a LASA drug pair may be referred to as a "LASA alternative drug name" with respect to the other member(s) of the pair. Each LASA alternative drug name may be associated with one or more drug products, referred to herein as LASA alternative drug products.

In certain embodiments, a submitted NDC# is mapped to a drug product and any LASA medication error screening is performed at the drug product level. Performing LASA medication error screening at the drug product level allows all brand name and generic versions of a particular drug product to be taken into account. For example, a prescription may have been written for an originally prescribed drug product (e.g., a brand name), but the pharmacist may specify the NDC# of a substitute drug product (e.g., a generic alternative) in the prescription transaction. While a LASA medication error may involve the originally prescribed drug product or the substitute drug product, screening on the NDC# level would only account for potential LASA medication errors involving the substitute drug product.

One screening process that may be employed is referred to herein as the "Absolute Dose Screening" process. The Absolute Dose Screening process determines if the calculated daily dose (i.e., quantity to be dispensed divided by days supply) of a prescription transaction exceeds the highest dose or falls below the lowest dose allowable for the drug product to be dispensed. When the calculated dosage fall outside the absolute dosing range, the drug name, dispense quantity and days supply should be verified. Absolute minimum dose values and absolute maximum dose values are determined from a review of manufacturers' labeling and standard reference texts and are intended to identify the extremes of the dosing range for drug products. Absolute minimum dose values and absolute maximum dose values may be stored in a database that is queried during the Absolute Dose Screening process.

Another screening process is referred to herein as the "Typical Dose Screening" process. Typical Dose Screening determines whether the calculated daily dose of a prescription transaction is typical or atypical for a given patient, as defined by actual prescribing patterns. The calculated daily dose is checked against "Common Daily Dose" values and "Most Common Daily Dose" values. These values may be derived from analysis of historical prescription transactions data for given drug products and may be stored in a database that is queried during the Typical Dose Screening process. When a calculated atypical daily dose is detected, a determination may be made as to whether the daily dose is typical for any LASA alternative drug products. If so, the pharmacist or other health care provider may be alerted as to the potential of a look-alike sound-alike medication error.

A further screening process is referred to herein as the "Likelihood Screening" process. Likelihood Screening determines a relative probability that a prescription transaction represents a potential look-alike sound-alike medication error. A drug product may be assigned a "Likelihood Indicator" in relation to each LASA drug pair with which it is associated. A Likelihood Indicator represents the likelihood of the drug product being incorrectly dispensed due to confusion caused by look-alike sound-alike medications. Likelihood Indicators may be stored in a database and may be pre-determined based on several factors, including but not limited to: similarity of drug names, frequency of dispense of drug products, similarity of strength as compared to LASA alternative drug product(s), same strength as compared to LASA alternative drug product(s), number of LASA pairs with which the drug product is associated, newness of the drug product to the marketplace and/or availability as non-solid oral products.

Exemplary embodiments of the present invention will hereinafter be described with reference to the figures, in which like numerals indicate like elements throughout the several drawings. FIG. 1 is a block diagram illustrating an exemplary operating environment for implementation of certain embodiments of the present invention. The exemplary operating environment encompasses a pharmacy point-of-service ("POS") device 102, a host server 104 and a payer system 108, which are each configured for accessing and reading associated computer-readable media having stored thereon data and/or computer-executable instructions for implementing the various methods of the present invention. Generally, network devices and systems include hardware and/or software for transmitting and receiving data and/or computer-executable instructions over a communications link and a memory for storing data and/or computer-executable instructions. Network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy POS device 102 may be in communication with the host server 104 via a network 106. The pharmacy POS device 102 may be configured for receiving prescription claim data, creating prescription transactions therefrom and transmitting said prescription transactions to the host server 104. Prescription claim data includes any data that is typically provided by a patient, pharmacist and/or other health care provider in relation to filling a prescription and/or requesting approval or authorization for payment from a payer or claim adjudicator. A payer may be an insurance company, a financial institution or another financial service provider. Prescription claim data may be input to the pharmacy POS device 102 by a pharmacist or other health care provider or may be received by the pharmacy POS device 102 in electronic form from an electronic prescription service (not shown). The pharmacy POS device 102 may be configured for handling other types of prescription transactions.

Prescription transactions are electronic records or messages intended to facilitate the communication of prescription information. For example, prescription claim transactions are intended to communicate prescription claim data between pharmacies and payers. Although prescription claim transactions will be discussed hereinafter, it should be understood that the various systems and method of the invention may be practiced in connection with other types of prescription transactions or independently of prescription transactions (e.g., raw prescription data). The content and format of a prescription claim may vary depending on which standard or protocol is used. In general, however, prescription claim transactions will identify at least the drug product to be dispensed (e.g., by NDC#), the quantity to be dispensed and the days supply, whether the prescription claim relates to a new prescription or a refill prescription and billing-related information.

Prescription claim transactions may be transmitted from the pharmacy POS device 102 to the host server 104 in batch, real-time or near real-time. In certain embodiments, the host server 104 may serve as a clearinghouse for multiple payer systems 108. Payer systems 108 may include systems operated by insurance companies, financial institutions and other financial service providers. In its capacity as a clearinghouse, the host server 104 parses prescription claim transactions and forwards them to the appropriate payer system 108 for processing. Approval, authorization or rejection messages may be returned to the host server 104 from the payer systems 108 and such messages may be forwarded by the host server 104 to the pharmacy POS device 102.

In serving as a clearinghouse, the host server 104 may also be configured for performing pre-processing and post-processing of prescription claim transactions. Pre-processing and post-processing refers to real-time or near real-time validation and management of prescription claim data in order to maximize prescription claim reimbursement and minimize claim submission errors. Pre-processing and post-processing may generate messaging alerts and/or retrospective reports supporting "usual and customary" price comparisons, average wholesale price ("AWP") edits, dispense as written ("DAW") brand appropriateness, and numerous other screening processes for facilitating rapid and accurate validation of prescription claims.

In accordance with the present invention, the host server 104 may be configured for performing certain screening processes for the detection of possible LASA medication errors. In the case where the host server 104 functions as a clearinghouse, the screening processes for detection of possible LASA medication errors may be implemented as pre-processing and/or post-processing methods. In other embodiments, the host server 104 may not serve as a clearinghouse for prescription claim transactions and may be dedicated to performing such tasks as LASA medication error screening. The LASA medication error screening processes of the present invention may be designed to generate alerts (also referred to as "Reject Messages") that are transmitted to the pharmacy POS device 102 when a potential LASA medication error is detected. Reject Messages may indicate that a prescription claim has been rejected, provide a pharmacist with information about the potential LASA medication error and may encourage the pharmacist to verify the prescription claim data. The LASA medication error screening processes are also designed to capture certain prescription claim data for subsequent analysis and reporting related to LASA medication errors.

The pharmacy POS device 102 may be any processor-driven device, such as a personal computer, laptop computer, handheld computer and the like. In addition to a processor 110, the pharmacy POS device 102 may further include a memory 112, input/output ("I/O") interface(s) 114 and a network interface 116. The memory 112 may store data files 118 and various program modules, such as an operating system ("OS") 120 and a practice management module 122. The practice management module 122 may comprise computer-executable instructions for performing various routines, such as those for creating and submitting prescription claim transactions. I/O interface(s) 114 facilitate communication between the processor 110 and various I/O devices, such as a keyboard, mouse, printer, microphone, speaker, monitor, etc. The network interface 116 may take any of a number of forms, such as a network interface card, a modem, etc. These and other components of the pharmacy POS device 102 will be apparent to those of ordinary skill in the art and are therefore not discussed in more detail herein.

Similarly, the host server 104 may be any processor-driven device that is configured for receiving and fulfilling requests related to prescription claim transactions. The host server 104 may therefore include a processor 126, a memory 128, input/output ("I/O") interface(s) 130 and a network interface 132. The memory 128 may store data files 134 and various program modules, such as an operating system ("OS") 136, a database management system ("DBMS") 138 and a LASA error messaging module 140. The LASA error messaging module 140 may comprise computer-executable instructions for performing various screening processes for detecting possible LASA medication errors and for managing related messaging and reporting functions. The host server 104 may include additional program modules (not shown) for performing other pre-processing or post-processing methods and for providing clearinghouse services. Those skilled in the art will appreciate that the host server 104 may include alternate and/or additional components, hardware or software. In addition, the host server 104 may be connected to a local or wide area network (not shown) that includes other devices, such as routers, firewalls, gateways, etc.

The host server 104 may include or be in communication with one or more database 105. The database 105 may store, for example, data relating to LASA drug pairs, Most Common Daily Dose values, Common Daily Dose values, Likelihood Indicators and other data used in the various LASA medication error screening processes of the present invention. The database 105 may also store reports and other data relating to the results of the LASA medication error screening processes. The database 105 may of course also store any other data used or generated by the host server 104, such as data used in other pre-processing and post-processing methods and reports generated thereby. Although a single database 105 is referred to herein for simplicity, those skilled in the art will appreciate that multiple physical and/or logical databases may be used to store the above mentioned data. For security, the host server 104 may have a dedicated connection to the database 105, as shown. However, the host server 104 may also communicate with the database 105 via a network 106.

The network 106 may comprise any telecommunication and/or data network, whether public or private, such as a local area network, a wide area network, an intranet, an internet and/or any combination thereof and may be wired and/or wireless. Due to network connectivity, various methodologies as described herein may be practiced in the context of distributed computing environments. Although the exemplary pharmacy POS device 102 is shown for simplicity as being in communication with the host server 104 via one intervening network 106, it is to be understood that any other network configuration is possible. For example, the pharmacy POS device 102 may be connected to a pharmacy's local or wide area network, which may include other devices, such as gateways and routers, for interfacing with another public or private network 106. Instead of or in addition to a network 106, dedicated communication links may be used to connect the various devices of the present invention.

Those skilled in the art will appreciate that the operating environment shown in and described with respect to FIG. 1 is provided by way of example only. Numerous other operating environments, system architectures and device configurations are possible. For example, the invention may in certain embodiments be implemented in a non-networked environment, in which a stand-alone pharmacy POS device 102 executes one or more LASA error messaging module(s) 140. Accordingly, the present invention should not be construed as being limited to any particular operating environment, system architecture or device configuration.

Figure 2:
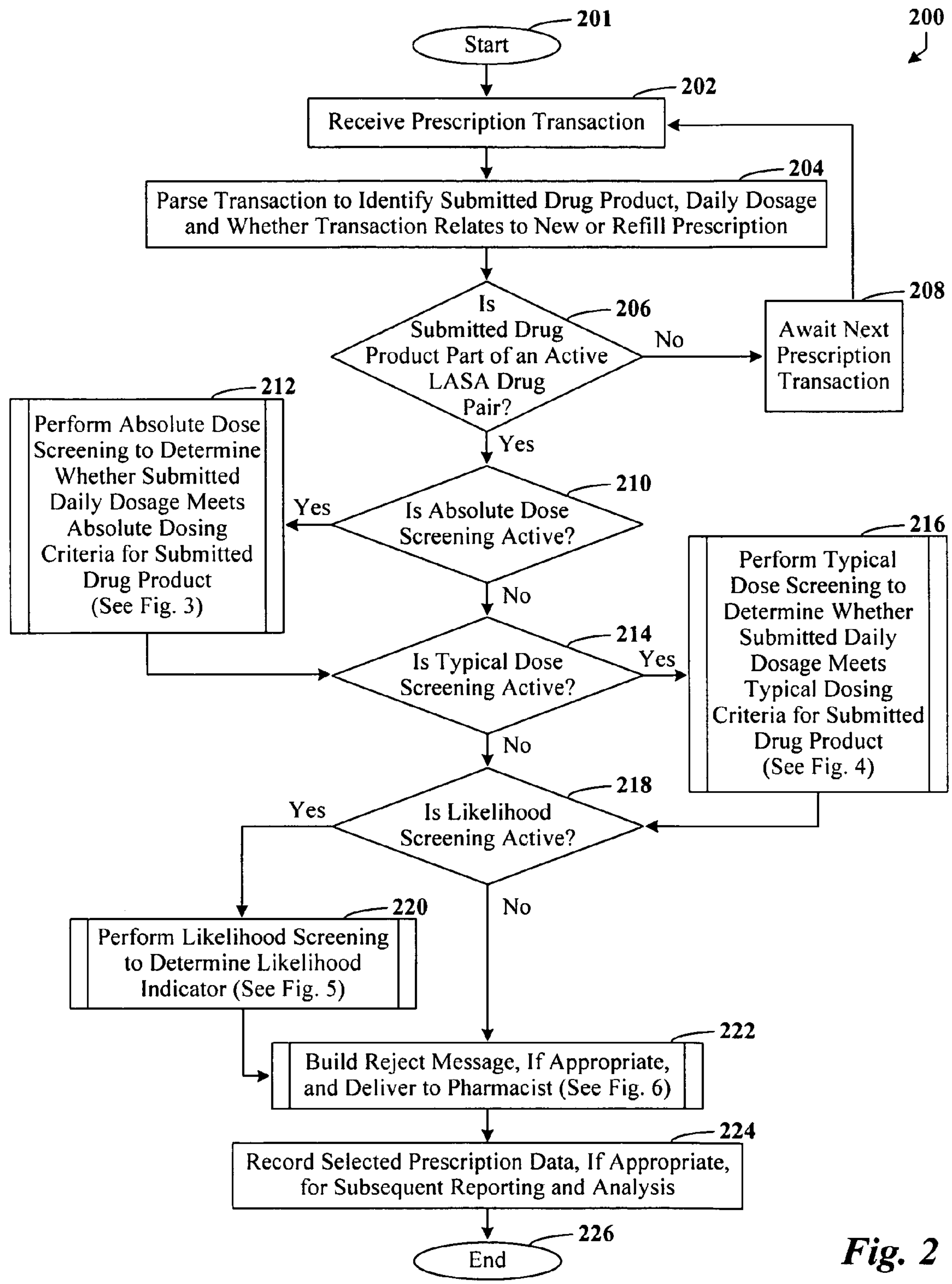
FIG. 2 is a flow chart illustrating an exemplary look-alike sound-alike medication error messaging method in accordance with certain exemplary embodiments of the present invention.

FIG. 2 is a flow diagram illustrating an exemplary process for screening prescription claims for potential LASA medication errors 200 in accordance with certain embodiments of the invention. The method begins at starting block 201 and progresses to step 202, where a prescription claim transaction is received. Next at step 204, the transaction is parsed to identify the submitted drug product, daily dosage and whether the transaction relates to a new prescription or a refill. The drug product and daily dosage values may be specified in the prescription claim transaction or may need to be derived from the prescription claim data. For example, the prescription claim data included in the transaction may include an NDC# or other code to identify the submitted drug product. In certain embodiments where LASA medication error screening is performed on the drug product level, a submitted NDC# is identified from the prescription claim data and a database 105 is queried to map the submitted NDC# to a drug product. The prescription claim data may also identify a quantity to be dispensed and a days supply, from which a submitted daily dosage value can be derived.

At step 206, a determination is made as to whether the submitted drug product is a member of an active LASA drug pair. The determination of step 206 may be made, for example, by interrogating a database 105 based on the submitted drug product. The database 105 may include a table populated with any or all available LASA drug pairs, each of which may be mapped to one or more drug products. LASA drug pairs may be defined or identified by an industry standards organization, such as USP, ISMP or FDA. LASA drug pairs may also be defined or identified by pharmaceutical companies, pharmacy managers, health care providers, etc.

In certain embodiments, each entry in a LASA drug pair database table may indicate whether the LASA drug pair is active or inactive. Active LASA drug pairs may be searched, while inactive LASA drug pairs may be ignored. A pharmacy manager or other system administrator may be provided with the ability to define whether a LASA drug pair is to be active or inactive and may thus be able to control which LASA drug pairs are to be included in the LASA medication error screening processes. Other embodiments may not distinguish between active and inactive LASA drug pairs, meaning that all LASA drug pairs in the database table are active and will be searched.

If the submitted drug product is not a member of an active LASA drug pair, the method proceeds to step 208 to await the next prescription claim transaction, the receipt of which will cause the method to be repeated, as described above, from step 202. However, if the submitted drug product is a member of an active LASA drug pair, the method advances to step 210 for a determination of whether the Absolute Dose Screening process is activated. As mentioned previously and described in greater detail below, Absolute Dose Screening may be used to determine whether the submitted daily dosage falls within a range defined by an absolute maximum dosage and an absolute minimum dosage for the submitted drug product. The Absolute Dose Screening process may be deactivated by the pharmacy manager or other system administrator.

If Absolute Dose Screening is activated, the method moves to step 212, where Absolute Dose Screening is performed in order to determine whether the submitted daily dosage meets the absolute dosing criteria for the submitted drug product. The Absolute Dose Screening process may generate an Absolute Dose Message to indicate whether the submitted daily dosage meets the absolute dosing criteria for the submitted drug product. Depending on a configurable "Edit Action" parameter of the Absolute Dose Screening process, any Absolute Dose Message may or may not be delivered to the pharmacist as part of a "Reject Message." Reject Messages may be used to indicate to the pharmacist that the prescription claim has been rejected for a particular reason, which may include non-compliance with absolute dosing criteria. The Absolute Dose Screening process may also specify that the Absolute Dose Message and/or certain prescription claim data should be captured for subsequent analysis and reporting.

In accordance with certain embodiments, Edit Action parameters may be used to define the situations in which a prescription claim should be rejected, the situations in which prescription claims transactions should be recorded for later analysis and reporting and the situations in which no action should be taken. In most cases, all rejected claims will likely be recorded. However, some claims may be recorded even if they are not rejected. For example, a prescription claim may violate absolute dosing criteria but for some reason (e.g., claim relates to a refill prescription) the claim may not be rejected. Such a claim may still be recoded for later analysis and reporting. In accordance with certain embodiments, the Edit Action parameters may be configured by the pharmacy manager or other system administrator.

After performance of Absolute Dose Screening at step 212, or if Absolute Dose Screening was determined to be inactive at step 210, the method advances to step 214 for a determination as to whether Typical Dose Screening is activated. As mentioned previously and described in greater detail below, Typical Dose Screening may be used to determine whether the submitted daily dosage is equivalent to statistically-determined Most Common Daily Dosage ("MCDD") or Common Daily Dosage ("CDD") values for the submitted drug product. If the submitted dosage is not equivalent to the MCDD for the submitted drug product, determinations may be made as to whether it is equivalent to the MCDD or CDD values for any LASA alternative drug product. If the submitted dosage is not equivalent to the MCDD for the submitted drug product, but is equivalent to the MCDD or CDD values for a LASA alternative drug product, a possible LASA medication error may exist. If the submitted dosage is not equivalent to the MCDD or CDD values for either the submitted drug product or any LASA alternative drug product, a dosing error may exist independent of a LASA medication error. The Typical Dose Screening process may be deactivated by the pharmacy manager or other system administrator.

If Typical Dose Screening is activated, the method moves to step 216, where Typical Dose Screening is performed in order to determine whether the submitted daily dosage meets the typical dosing criteria for the submitted drug product. The Typical Dose Screening process may generate a Typical Dose Message to indicate whether the submitted daily dosage meets the typical dosing criteria for the submitted drug product. Depending on a configurable "Edit Action" parameter of the Typical Dose Screening process, any Typical Dose Message may or may not be delivered to the pharmacist as part of a Reject Message. The Typical Dose Edit Action may also specify that the Typical Dose Message and/or certain prescription claim data should be captured for subsequent analysis and reporting.

After performance of Typical Dose Screening at step 216, or if Typical Dose Screening was determined to be inactive at step 214, the method advances to step 218 for a determination as to whether Likelihood Screening is activated. As mentioned previously and described in greater detail below, Likelihood Screening may be used to determine a relative probability that a prescription claim includes a potential LASA medication error. The Likelihood Screening process may be deactivated by the pharmacy manager or other system administrator.

If Likelihood Screening is activated, the method moves to step 220, where Likelihood Screening is performed in order to determine a Likelihood Indicator for the submitted drug product in relation to each LASA drug pair with which the submitted drug product is associated. The Likelihood Screening process may generate a Likelihood Message based on a Likelihood Indicator. Depending on a configurable "Edit Action" parameter of the Likelihood Screening process, any Likelihood Message may or may not be delivered to the pharmacist as part of a Reject Message. The Likelihood Edit Action may also specify that the Likelihood Message and/or certain prescription claim data should be captured for subsequent analysis and reporting.

After performance of Likelihood Screening at step 220, or if Likelihood Screening was determined to be inactive at step 218, the method advances to step 222 where a Reject Message is built, if appropriate. In exemplary embodiments, a Reject Message may be built when an Edit Action parameter from at least one of the screening processes indicates that the prescription claim should be rejected. If the Absolute Dose Edit Action indicates that the prescription claim should be rejected, the Absolute Dose Message may be inserted into the Reject Message. If the Typical Dose Edit Action indicates that the prescription claim should be rejected, the Typical Dose Message may be inserted into the Reject Message. If the Likelihood Edit Action indicates that the prescription claim should be rejected, the Likelihood Message may be inserted into the Reject Message.

However, inclusion of multiple messages in a Reject Message may be redundant or otherwise unnecessary. Therefore, if the prescription claim transaction is to be rejected based on the results of multiple screening processes, logic may be employed to prioritize and select the message or messages to be included in the Reject Message. After a Reject Message is built, it is delivered to the pharmacist. In exemplary embodiments, Reject Messages are delivered to the pharmacist in the form of electronic messages to the practice management module 122 executed by the pharmacy POS device 102. Such electronic messages may be delivered via the network 106 as propagated signals.

Next, the method proceeds to step 224, where selected messages and/or prescription claim data is recorded, if appropriate, for subsequent reporting and analysis. Again, whether or not recording of prescription claim data is appropriate may be conditioned on the Edit Action parameters that were returned by each screening process. If at least one Edit Action parameter indicates that the prescription claim should be rejected, prescription claim data and/or appropriate message(s) should be recorded. Also, if at least one Edit Action parameter indicates that the prescription claim should be captured (i.e., recorded but not rejected), such action should be taken. If all Edit Action parameters indicate that no action should be taken for the prescription claim, then no prescription claim data or messages are recorded. Edit Action parameters may also dictate which prescription claim data is to be recorded. For example, different data may need to be recorded for reporting and analysis of non-compliance with typical dosing criteria than may need to be recorded for reporting and analysis of non-compliance with absolute dosing criteria.

Following step 224, the method ends at step 226. Those skilled in the art will appreciate that other screening processes, in addition to Absolute Dose Screening, Typical Dose Screening and Likelihood Screening may be incorporated into the overall method 200 of the present invention. The above-mentioned analysis and reporting of recorded prescription claim data may be performed on all recorded data in order to form generalized conclusions regarding LASA medication errors. Alternatively, the recorded data may be analyzed at the pharmacy chain level, pharmacy store level, physician level, patient demographic grouping level, etc. in order to form more specific conclusions regarding LASA medication errors.

Although not illustrated in FIG. 2, it should be appreciated that the systems and methods of the present invention may be configured to accept "overrides" from pharmacists or system administrator. In other words, a pharmacist or system administrator may be able to override a rejection of a prescription claim and cause the prescription claim to be processed. The pharmacists or system administrator may need to provide a code or some other identifier that indicates his/her authority to request the override. The pharmacist may need to change some portion of the prescription claim data in order to request an override. In certain embodiments, if an override is submitted, any messages previously produced by the LASA medication error screening processes may be attached to post-edit message delivered to the pharmacist.

Edit overrides and transactions resulting therefrom may also be recorded for subsequent reporting and analysis. Comparison of all versions of a particular prescription claim through a process known as "Prescription Matching" can provide useful insight into the reason(s) why the pharmacist may have made an error or why the reject message was a false positive. Prescription Matching involves identifying all prescriptions claims having the same date of service and prescription number from the same pharmacy. The latest such prescription claim is designated as the "Matching Prescription" and is given a key to link it back to prior version(s) of the transaction that invoked the reject message.

The systems and methods of the present invention may be configured with an "Always Message" option for certain types of prescription claim transactions. In an Always Message mode, the LASA medication error screening processes may be skipped and an administratively-defined message may be sent to the pharmacist. For example, the Always Message mode may be configured to send a customized warning message to a pharmacist every time a particular drug product is identified in a prescription claim transaction. Prescription claim data may be captured for reporting and analysis in an Always Message situation.

Figure 3:
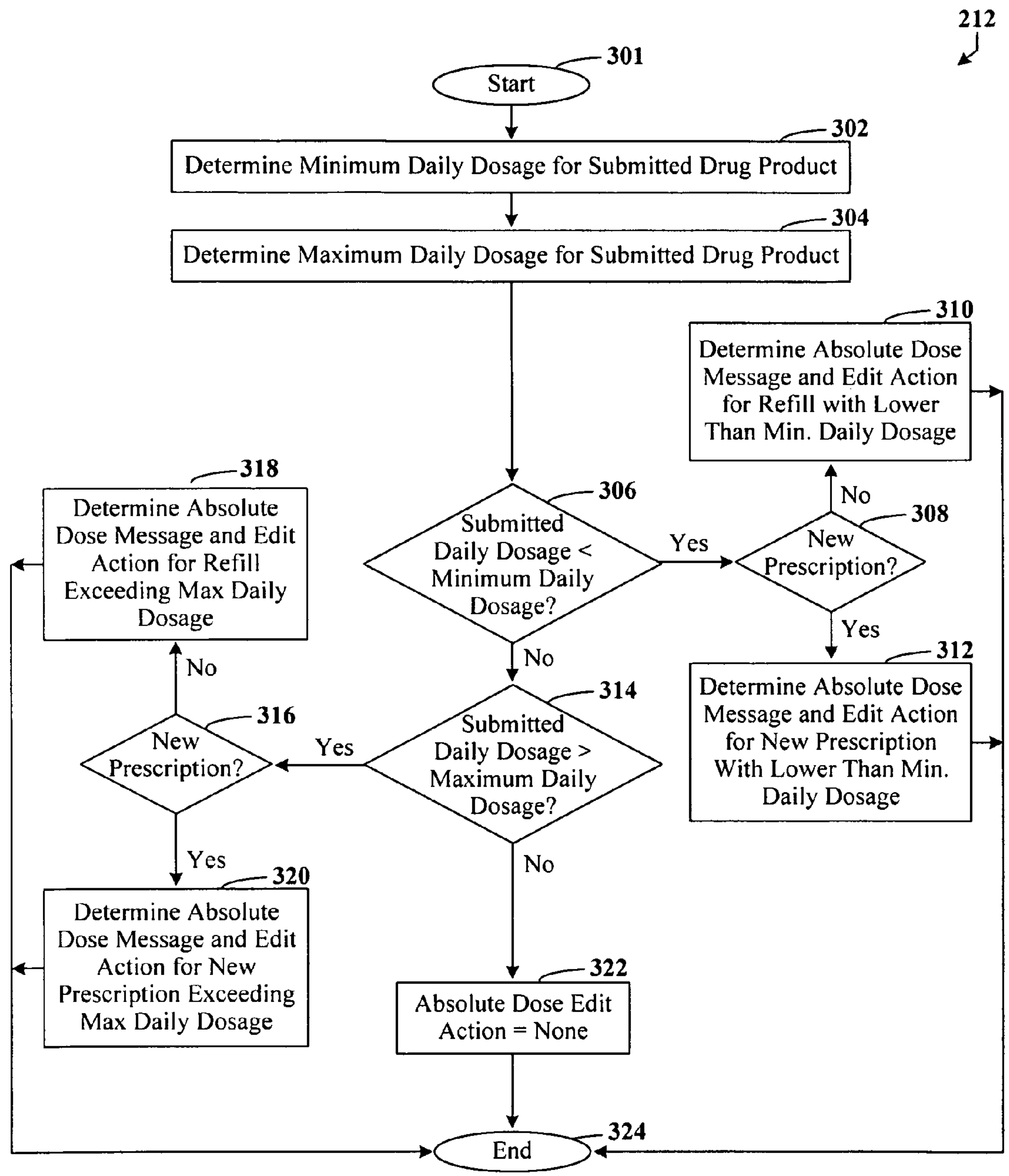
FIG. 3 is a flow chart illustrating an exemplary Absolute Dose Screening process in accordance with certain exemplary embodiments of the present invention.

FIG. 3 is a flow chart illustrating an exemplary Absolute Dose screening process 212 in accordance with one or more embodiments of the present invention. The Absolute Dose screening process 212 begins at starting block 301 and then proceeds to step 302, where the absolute minimum doses per day for the submitted drug product is determined. The absolute minimum doses per day may be determined by interrogating a database storing such information. Absolute minimum daily dosages are defined by various text references known in the health care industry, such as the Physicians Desk Reference ("PDR"), the United States Pharmacopedia Drug Information ("USPDI") and the like, as well as by the United States Food and Drug Administration ("USFDA"). Next at step 304, the absolute maximum doses per day for the submitted drug product is determined. Again, information regarding maximum daily dosages for drug products may be stored in and retrieved from a database.

At step 306 a determination is made as to whether the submitted doses per day is less than the absolute minimum doses per day for the submitted drug product. If so, the method proceeds to step 308 for a determination of whether the prescription claim relates to a new prescription. If the prescription does not relate to a new prescription, the method moves to step 310 to determine the Absolute Dose Message and the administratively-defined Absolute Dose Edit Action for refills with lower than the absolute minimum daily dosage. If the prescription does relate to a new prescription, the method moves to step 312 to determine the Absolute Dose Message and the administratively-defined Absolute Dose Edit Action for new prescriptions with lower than the absolute minimum daily dosage. After determining an Absolute Dose Message and an Absolute Dose Edit Action at either step 310 or step 312, the method ends at step 324.

As mentioned previously, Absolute Dose Messages may be used to indicate whether the submitted daily dosage meets the absolute dosing criteria for the submitted drug product. Absolute Dose Messages may take any appropriate form and may be used, for example, to inform or remind the pharmacist of the absolute maximum or minimum dosages for the submitted drug product. In accordance with certain embodiments, Edit Action options may be: "Reject," "Capture" and "None." The Reject Edit Action may be used to indicate that the Absolute Dose Message should be included in a Reject Message sent to the pharmacist. The Capture Edit Action may be used to indicate that the Absolute Dose Message and other prescription claim transaction data should be recorded for later analysis, but not included in a Reject Message. The None Edit Action may be used to indicate that no recording or Reject Message is required. Other Edit Actions are possible. For example, an Edit Action may be defined to indicate that the Absolute Dose Message should be sent to the pharmacist as an information message when the prescription claim is not rejected. Or, an Edit Action may be defined to indicate that the Absolute Dose Message should be printed on a warning label.

These and other examples of Edit Actions are contemplated in connection with all screening processes of the present invention.

Edit Actions are referred to as being administratively-defined because a system administrator, such as a pharmacy manager, may determine which Edit Action is applicable to a given situation. As an example, for various reasons one system administrator may determine that a Reject Edit Action is appropriate when a prescription claim transaction relates to a refill with lower than the absolute minimum daily dosage. Another system administrator may determine that a Capture Edit Action is appropriate for the same situation. Edit Actions for given situations may be re-set at any time. For example, if it is determined that a Reject Edit Action for a particular situation yields too may "false positive" LASA medication errors, the Edit Action for that situation may be changed to Capture.

Absolute Dose Messages and Absolute Dose Edit Actions may be stored in one or more look-up tables or other suitable data structures within a database 105 accessible by the host server 104. Table 1 below is an example of such a look-up table. Table 1 is provided by way of illustration only. Other Absolute Dose Messages and/or Absolute Dose Edit Actions may be used in situations where a submitted daily dosage exceeds an absolute maximum daily dosage or is less than an absolute minimum daily dosage.

TABLE 1

Absolute Dose Messages and Edit Actions

| Submitted Daily Dosage | New Rx | Refill Rx | Absolute Dose Message: |
|---|---|---|---|
| <Absolute Min | Edit Action = Reject | Edit Action = None | "[XXX] Doses/Day Minimum" |
| >Absolute Max | Edit Action = Reject | Edit Action = None | "[XXX] Doses/Day Maximum" |

Returning to step 306, if it is determined that the submitted doses per day is not less than the absolute minimum doses per day for the submitted drug product, the method proceeds to step 314 for a determination of whether the submitted doses per day is greater than the absolute maximum doses per day for the submitted drug product. If the submitted doses per day is greater than the absolute maximum doses per day for the submitted drug product, the method proceeds to step 316, where a determination is made as to whether the prescription claim relates to a new prescription. If the prescription does not relate to a new prescription, the method moves to step 318 to determine the Absolute Dose Message and the administratively-defined Absolute Dose Edit Action for refills exceeding the absolute maximum daily dosage. If the prescription does relate to a new prescription, the method moves to step 320 to determine the Absolute Dose Message and the administratively-defined Absolute Dose Edit Action for new prescriptions exceeding the absolute maximum daily dosage. Again, Absolute Dose Messages and Absolute Dose Edit Actions may be determined by consulting a look-up table, such as the above-illustrated Table 1, or other data structure containing such information. After determining an Absolute Dose Message and an Absolute Dose Edit Action at either step 318 or step 320, the method ends at step 324.

If at step 314 it is determined that the submitted doses per day is not greater than the absolute maximum doses per day for the submitted drug product, the submitted doses per day satisfies the absolute dosing criteria for the submitted drug product. In that case, the method moves to step 322 where the Absolute Dose Edit Action is set to None. Following step 322, the method ends at step 324.

Figure 4:
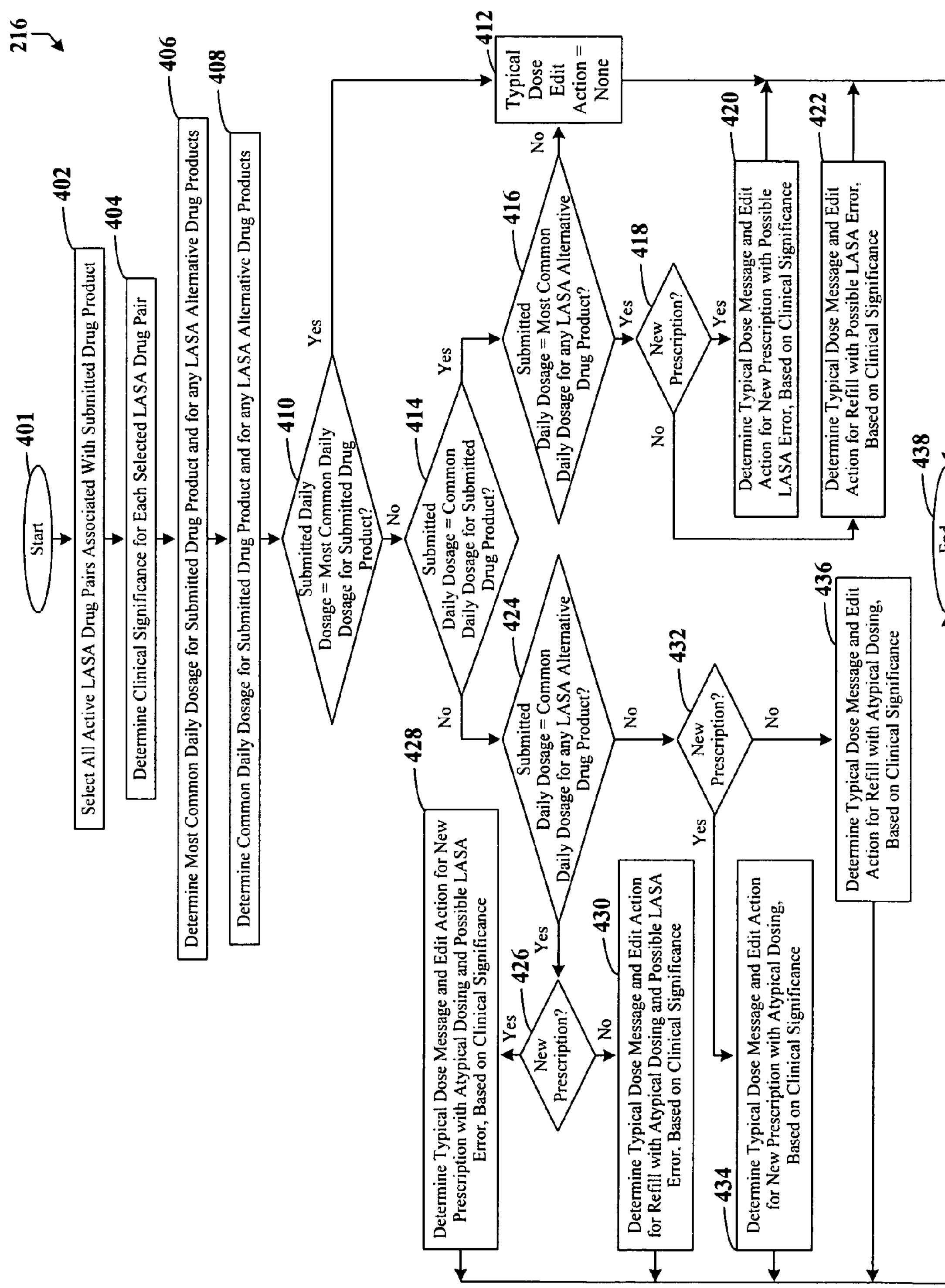
FIG. 4 is a flow chart illustrating an exemplary Typical Dose Screening process in accordance with certain exemplary embodiments of the present invention.

FIG. 4 is a flow chart illustrating an exemplary Typical Dose screening process 216 (from FIG. 2) in accordance with one or more embodiments of the present invention. The Typical Dose screening process 216 begins at starting block 401 and then proceeds to step 402, where the all active LASA drug pairs associated with the submitted drug product are selected. As mentioned previously, a list or table of LASA drug pairs may be stored in a database 105. A system administrator, such as a pharmacy manager, may specify which of the LASA drug pairs is to be considered "active" and therefore examined during the Typical Dose Screening process 216. It is assumed, based on the flow of FIG. 2, that the submitted drug product is associated with at least one active LASA drug pair; if not, the Typical Dose Screening process 216 would not be performed. However, those skilled in the art will appreciate that the Typical Dose Screening process 216 may be used outside the context of FIG. 2 and could thus be modified to include a database check for at least one active LASA drug pair associated with the submitted drug product.

After selecting all active LASA drug pair associated with the submitted drug product, the method advances to step 404, where the clinical significance for each selected LASA drug pair is determined. Clinical significance values may be stored in a database 105 in association with corresponding LASA drug pairs and may be modified as appropriate. Clinical significance may be represented by a clinically-determined value assigned to a LASA drug pair. Clinical significance may be used to quantify the consequences of a LASA medication error caused by substituting one drug product associated with the LASA drug pair with a LASA alternate drug product associated with the LASA drug pair. For example, a clinical significance of 1 may be used to indicate that a LASA medication error could be harmful or fatal; a clinical significance of 2 may be used to indicate that a LASA medication error could have a mild effect on the patient; and a clinical significance of 3 may be used to indicate that a LASA medication error could little or no effect on the patient. Clinical significance values may be determined in numerous manners and may be derived from clinical data, knowledge and/or expertise.

After determining the clinical significance values, the method proceeds to step 406 to determine the Most Common Daily Dosage ("MCDD") values for the submitted drug product and for any LASA alternative drug products associated with the selected LASA drug pairs. Next at step 408, Common Daily Dosage ("CDD") values are determined for the submitted drug product and for any LASA alternative drug products associated with the selected LASA drug pairs. MCDD values and CDD values may be determined at step 406 and 408 by consulting a look-up table or other suitable data structure (e.g., stored in database 105) containing such information. Those skilled in the art will appreciate that steps 402, 404, 406 and 408 may be performed in a different order, simultaneously, etc.

MCDD and CDD values may be derived in a variety of ways, such as through statistical analysis of historical prescription claim data. Those skilled in the art will appreciate that suitable statistical analysis methods include, but are not limited to, cluster analysis, logistic regression, Chi-square tests and Graphing methods. Historical prescription claims data may be analyzed using one or more of such methods, or other suitable methods, in order to identify actual prescribing patterns for drug products, from which statistically valid CDD and MCDD values can be derived. Depending on the criteria used to define CDD and MCDD values, a given drug product may have more than one CDD. Likewise, a given drug product may not have a CDD or an MCDD.

By way of illustration only and not by way of limitation, CDD and MCDD values may be derived as follows. A sample of not less than a predetermined number (e.g., 100) of prescription claim transactions involving a given drug product may be analyzed to identify historical prescribing patterns for the drug product. If a particular daily dose +/−a deviation (e.g., 0.15 units) is determined to have been prescribed in a predetermined percentage (e.g., 10% or more) of all transactions in the sample, then that daily dose constitutes a CDD. If a first CDD is a daily dosage that was prescribed in a second predetermined percentage (e.g., 50% or more) of all transactions in the sample and a second CDD is significantly different from the first CDD (e.g., by Chi Square test for equal proportions in two runs of 25 randomly selected transactions), then the first CDD is the MCDD for the drug product. If a first CDD is a daily dosage that was prescribed in a third predetermined percentage (e.g., greater than 50%) of the transactions in the sample and a second CDD is found that is not significantly different from the first CDD (e.g., by Chi Square test for equal proportions in two runs of 25 randomly selected transactions), then no MCDD exists.

In certain embodiments, CDD and/or MCDD values for a drug product may be tied to one or more patient demographic groups, such as those based on gender or age. In other words, the CDD and/or MCDD values for a given drug product may be different for different types of patient demographic groups. As an example, a drug product may have a MCDD value for women that is different from its MCDD value for men. Patient demographic group characteristics may thus be built into the statistical analysis model(s) used to derive CDD and MCDD values from historical prescription claims data.

At step 410 a determination is made as to whether the submitted daily dosage is equal to the MCDD for the submitted drug product. If the submitted daily dosage is equal to the MCDD for the submitted drug product, the method moves to step 412, where the Typical Dose Edit Action for the transaction is set to "None." Following step 412, the method ends at step 438. However, if it is determined at step 410 that the submitted daily dosage is not equal to the MCDD for the submitted drug product, the method proceeds to step 414, where a determination is made as to whether the submitted daily dosage is equal to the CDD for the submitted drug product.

If the submitted daily dosage is equal to the CDD for the submitted drug product, the method advances to step 416, where it is determined whether the submitted daily dosage is equal to the MCDD for any LASA alternative drug product associated with the selected LASA drug pairs. If the submitted daily dosage is not equal to the MCDD for any LASA alternative drug product associated with the selected LASA drug pairs, the method moves to step 412, where the Typical Dose Edit Action for the prescription claim is set to "None." Following step 412, the method ends at step 438. If, however, the submitted daily dosage is determined at step 416 to be equal to the MCDD for any LASA alternative drug product, a potential LASA medication error is deemed to have been identified and the method proceeds to step 418.

The particular Typical Dose Message and Typical Dose Edit Action to be applied may depend on whether the submitted prescription claim relates to a new prescription or to a refill prescription. Also, the Typical Dose Message and Typical Dose Edit Action to be applied may depend on the clinical significance assigned to the involved LASA drug pair. Thus, at step 418, a check is made to determine whether the prescription claim relates to a new prescription. If the prescription claim relates to a new prescription, the method proceeds to step 420, where the Typical Dose Message and Typical Dose Edit Action are determined for a new prescription with a possible LASA medication error, based on clinical significance. If the prescription claim does not relate to a new prescription, the method proceeds to step 422 where the Typical Dose Message and Typical Dose Edit Action are determined for a refill prescription with a possible LASA medication error, based on clinical significance.

To determine applicable Typical Dose Messages and Typical Dose Edit Actions, a look-up table or other data structure containing such information may be consulted. An exemplary look-up table is illustrated below as Table 2.

TABLE 2

Typical Dose Messages and Edit Actions

| Submitted Drug Product | Alternate Drug Product | Clinical Significance | New Rx | Refill Rx | Typical Dose Message |
|---|---|---|---|---|---|
| MCDD | — | — | Edit Action = None | Edit Action = None | — |
| CDD | MCDD | 1 | Edit Action = Reject | Edit Action = None | "Possible LASA w/ [LASA Alternative Drug Name(s)]" |
| CDD | MCDD | 2 | Edit Action = Capture | Edit Action = None | "Possible LASA w/ [LASA Alternative Drug Name(s)]" |
| CDD | MCDD | 3 | Edit Action = Capture | Edit Action = None | "Possible LASA w/ [LASA Alternative Drug Name(s)]" |
| Atypical | CDD | 1 | Edit Action = Reject | Edit Action = None | "Atypical Doses/Day-Check for LASA w/ [LASA Alternative Drug Name(s)]" |
| Atypical | CDD | 2 | Edit Action = Reject | Edit Action = None | "Atypical Doses/Day-Check for LASA w/ [LASA Alternative Drug Name(s)]" |

TABLE 2-continued

Typical Dose Messages and Edit Actions

| Submitted Drug Product | Alternate Drug Product | Clinical Significance | New Rx | Refill Rx | Typical Dose Message |
|---|---|---|---|---|---|
| Atypical | CDD | 3 | Edit Action = Reject | Edit Action = None | "Atypical Doses/Day-Check for LASA w/ [LASA Alternative Drug Name(s)]" |
| Atypical | Atypical | 1 | Edit Action = None | Edit Action = None | "Atypical Doses/Day-Check Dosing" |
| Atypical | Atypical | 2 | Edit Action = None | Edit Action = None | "Atypical Doses/Day-Check Dosing" |
| Atypical | Atypical | 3 | Edit Action = None | Edit Action None | "Atypical Doses/Day-Check Dosing" |

Table 2 above, is shown by way of example only. Other Typical Dose Messages and Typical Dose Edit Actions may be associated with clinical significance values and CDD/MCDD/Atypical situations. Table 2 illustrates one fictitious system administrator's desire to reject a prescription claim when the submitted daily dosage is equal to the CDD for the submitted drug product and the clinical significance value is "1 " or when the submitted daily dosage is atypical for the submitted drug product, but is equal to the CDD for a LASA alternative drug product associated with the selected LASA drug pairs. In the case where the submitted daily dosage is equal to the MCDD for the submitted drug product, a Typical Dose Message so indicating may be used, or no Typical Dose Message may be used. Multiple LASA alternative drug names may be inserted into the Typical Dose Message and may be ordered according to clinical significance. In certain embodiment, all LASA alternative drug names are inserted if the submitted daily dosage is equal to the MCDD or CDD for any one LASA alternative drug product associated with the selected LASA drug pairs.

Returning to step 414 if the submitted daily dosage is determined to not be equal to the CDD for the submitted drug product, the method proceeds to step 424, where it is determined whether the submitted daily dosage is equal to the CDD for any LASA alternative drug product associated with the selected LASA drug pairs. If the submitted daily dosage is equal to the CDD for any LASA alternative drug product, a potential LASA medication error is deemed to have been identified and the method proceeds to step 426. At step 426, a check is made to determine whether the prescription claim relates to a new prescription. If the prescription claim relates to a new prescription, the method proceeds to step 428 where the Typical Dose Message and Typical Dose Edit Action are determined for a new prescription with atypical dosing and a possible LASA error, based on clinical significance.

If the prescription claim does not relate to a new prescription, the method proceeds to step 430 where the Typical Dose Message and Typical Dose Edit Action are determined for a refill prescription with atypical dosing and a possible LASA error, based on clinical significance. Again, Typical Dose Messages and Typical Dose Edit Actions may be determined by querying a look-up table, such as Table 2, or other data structure containing such information. After determining a Typical Dose Message and Typical Dose Edit Action at either step 428 or step 430, the method ends at step 438.

However, if it is determined at step 424 that the submitted daily dosage is not equal to the CDD for any LASA alternative drug product, no potential LASA medication error is deemed to have been identified. In that case, the method proceeds to step 432, where a check is made as to whether the prescription claim relates to a new prescription. If the prescription claim relates to a new prescription, the method proceeds to step 434 where the Typical Dose Message and Typical Dose Edit Action are determined for a new prescription with atypical dosing, based on clinical significance. If the prescription claim does not relate to a new prescription, the method proceeds to step 436 where the Typical Dose Message and Typical Dose Edit Action are determined for a refill prescription with atypical dosing, based on clinical significance. Typical Dose Messages and Typical Dose Edit Actions may be determined, for example, from a look-up table, such as Table 2, or another data structure containing such information. After determining a Typical Dose Message and Typical Dose Edit Action at either step 434 or step 436, the method ends at step 438.

In other embodiments, the Typical Dose Screening process may be adapted for use outside of the context of LASA medication error screening. For example, a prescription claim transaction may be parsed to identify a submitted drug product and a submitted daily dosage. It may then be determined whether the submitted daily dosage meets statistically derived typical dosing criteria (e.g., a CDD) for the submitted drug product. If the submitted daily dosage does not meet the statistically derived typical dosing criteria for the submitted drug product a Typical Dose Message may be determined. In such an embodiment, a Typical Dose Edit Action may be determined based on whether the prescription claim relates to a new prescription or a refill.

Figure 5:
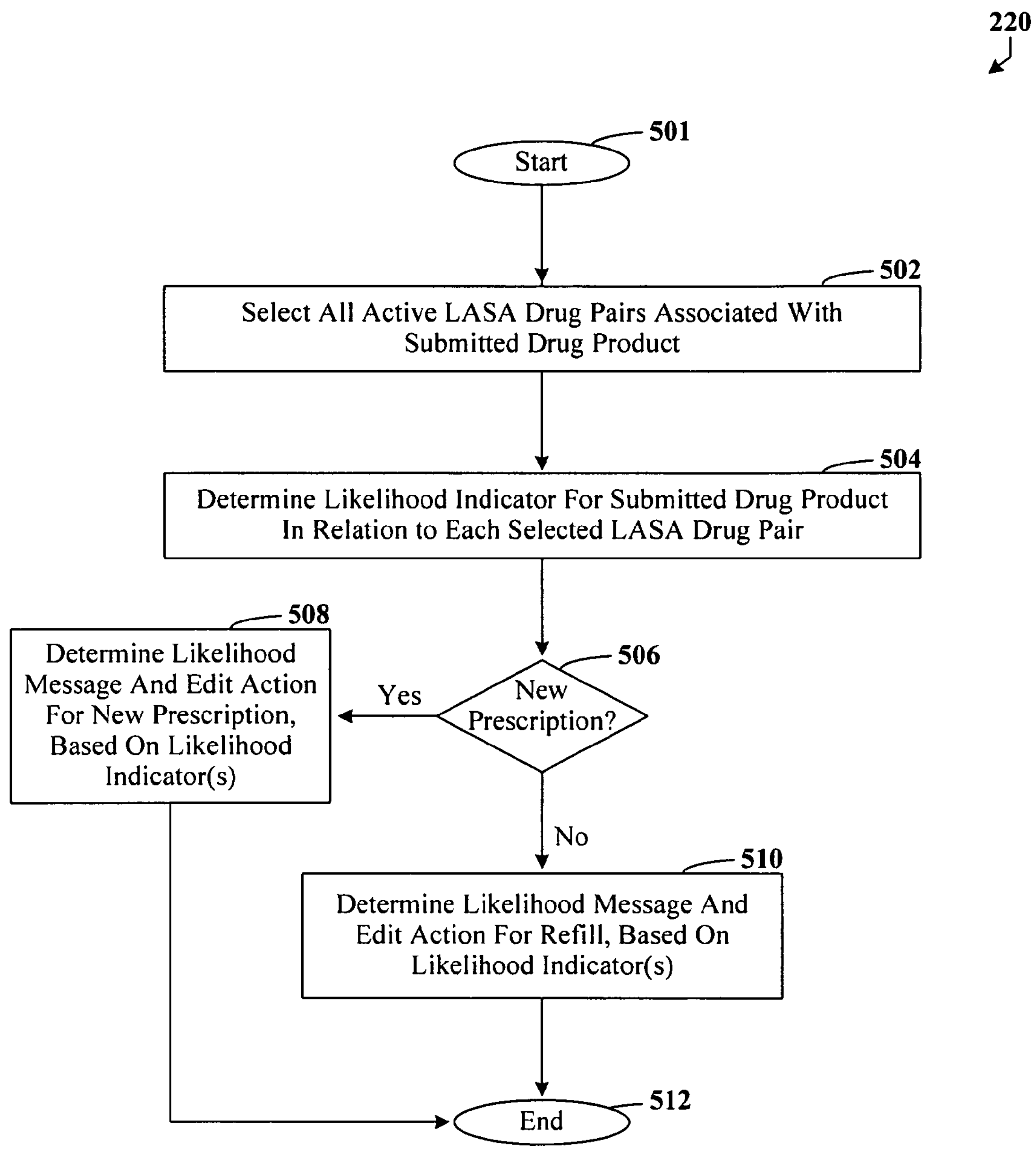
FIG. 5 is a flow chart illustrating an exemplary Likelihood Screening process in accordance with certain exemplary embodiments of the present invention.

FIG. 5 is a flow chart illustrating an exemplary Likelihood Screening process 220 (from FIG. 2) in accordance with certain embodiments of the present invention. The exemplary Likelihood Screening process seeks to determine one or more Likelihood Indicators for the submitted drug product, which are used to determine a Likelihood Message. A Likelihood Indicator is meant herein to represent a relative probability of whether a submitted drug product is involved in a LASA medication error involving an associated LASA drug pair. Likelihood Indicators may be pre-determined and stored in a database in association with drug products, meaning that they are not dynamically determined each time the exemplary Likelihood Screening process 220 is executed. Thus, during execution of the Likelihood Screening process, a database may be queried to retrieve the Likelihood Indicator(s) for a given drug product.

A variety of factors may contribute to whether a LASA medication error is likely. Research has indicated that three significant contributors to the likelihood of a LASA medication error involving a pair of drugs are: (1) the degree to which the drug names look or sound alike; (2) whether one drug is available in a same-strength, a look-alike strength or a sound-alike strength as the other drug; and (3) differing degrees of familiarity that a pharmacist may have with the drugs, resulting in confirmation bias. Other factors may enhance the likelihood of a LASA medication error involving a pair of drug, including but not limited to, whether both drugs are available in the same dosage form and whether both drugs are available in non-oral solid dosage form.

Still other factors may diminish the likelihood of a LASA medication error. These diminishing factors include, but are not limited to, very different dispensing requirements between the drugs; any action taken by the drug manufacturer to decrease likelihood of error (e.g., change in packaging); a low number of different LASA drug pairs in which a drug name is included; a low market share for a drug having a branded generic name; a generic drug name of a single-source brand, which is very unlikely to be prescribed by generic drug name except in hospital setting.

Levenshtein Distance (LD) may be used to predict whether a pair of drug names are sufficiently similar to give rise to a LASA medication error. Levenshtein Distance is a measure of the similarity between two strings, which are referred to herein as the “source string” and the “target string.” The LD is defined as the number of deletions, insertions, or substitutions required to transform the source string into the target string. For example, if the source string is “test” and the target string is also “test,” then LD(source, target)=0 because no transformations are needed to conform the strings. If the source string is “test” and the target string is “tent”, then LD(source, target)=1, because one substitution (changing the letter “s” to the letter “n”) is sufficient to transform the source string into the target string. The greater the Levenshtein distance, the more different the strings are.

In accordance with certain embodiments, a Threshold LD may be defined as the LD between two drug names below which a LASA medication error is likely. For example, the Threshold LD may be set to 5 or another administratively defined value. In the case where the Threshold LD is 5, the drug names Serzone and sertraline, which have an LD of 7, would not be considered similar enough to give rise to a LASA medication error, based on LD alone. For two-part words separated by a space or hyphen, LD may be calculated with and without the divider and the greater of the LD may be ignored. For parts of drug names that could be noted different ways (e.g., “24-hour” v. “24 hr” v. “24 h”) the shortest notation may be used in calculating LD, along with the two-part rule, if necessary. Other tests for determining similarity in sound and/or appearance between words are known in the art and may be substituted and/or used in conjunction with the Levenshtein Distance test.

In certain embodiments, the prescribing frequency will be determined at the generic level, but exceptions may be made for cases where the prescribing frequency of an individual drug product is not reflective of the frequency for the generic level. Prescribing frequencies may be categorized as either “High,” “Medium” or “Low.” The dividing lines between High, Medium and Low prescribing frequencies may be different in different embodiments. As one example, a High prescribing frequency may assigned to drug products that account for the top 50% of the total prescriptions for the set of all drug products associated with the LASA drug pair list. More particularly, the total prescription count for all such drug products may be determined. Then all drug products may be ranked in descending order by prescription count and a cumulative percent and cumulative total may be determined for each drug product. All drug products with a cumulative percentage of 50% or greater are assigned a High prescribing frequency, while all drug products with a cumulative percentage of 0.25% or less is assigned a Low prescribing frequency. Each drug product falling in between the High and Low categories is assigned a Medium prescribing frequency. The number of total prescriptions may be based on prescriptions per pharmacist, per pharmacy or per multiple pharmacies.

In certain embodiments, a drug name of a LASA drug pair may be assigned a High prescribing frequency if any associated drug product has a High prescribing frequency. Similarly, a drug name of a LASA drug pair may be assigned a Medium prescribing frequency if no associated drug product has a High prescribing frequency but at least one associated drug product has a Medium prescribing frequency. A drug name of a LASA drug pair may be assigned a Low prescribing frequency if no associated drug product has a High or a Medium prescribing frequency. It may be assumed that a LASA drug pair having a High-Low combination of prescribing frequencies has the potential for confirmation bias. In other words, a pharmacist may mistakenly attempt to dispense a first drug having a High prescribing frequency instead of a second drug having a Low prescribing frequency simply because he or she is more accustomed to dealing with the first drug. It may also be assumed that a LASA drug pair having a Low-Low combination of prescribing frequencies has the potential for confirmation bias because any individual pharmacist may have heard of one such drug but not the other. Different assumptions regarding confirmation bias may be drawn in other embodiments.

As used herein, the term “same-strength” refers to strength indicators (e.g., 5 mg) that are identical. Look-alike strengths are considered to be any strength indicators with the same series of numbers, regardless of leading or following zeros or decimal points. For example, 0.5 mg, 5 mg, 50 mg and 500 mg are considered to be look-alike strengths. Since decimal points can sometimes be mistaken for ones, strength indicators such as 0.5 and 15, for example, could also be considered look-alike strengths in certain embodiments. Sound-alike strengths are considered to be any strength indicators that sound similar when spoken. An example of sound-alike strengths are 15 mg and 50 mg.

Exemplary criteria for determining Likelihood Indicators in accordance with certain embodiments of the invention are summarized in Table 3 below. It is to be understood, however, that Table 3 is provided by way of illustration only. Other criteria or combinations of criteria may be used to determine the likelihood of a LASA medication error. In addition, different weights (levels of perceived significance) may be assigned to the described and other criteria.

TABLE 3

Likelihood Indicator Look-Up Table

| Likelihood Indicator | Criteria |
|---|---|
| 1 | A AND B AND C<br>OR Any Two Of A, B Or C If Both LASA Drug Pair Members Have Same Dosage Form That Is NOT An Oral Solid AND No Decreasing Factors Are Present. |
| 2 | (A AND B) OR (B AND C) OR (A AND C)<br>OR Any One Of A, B, Or C if Both LASA Drug Pair Members Have Same Dosage Form That Is NOT An Oral Solid AND No Decreasing Factors Are Present |
| 3 | A OR B OR C<br>OR None Of A, B Or C Is True AND Both LASA Drug Pair Members Have Same Dosage Form That Is NOT An Oral Solid AND No Decreasing Factors Are Present |

TABLE 3-continued

Likelihood Indicator Look-Up Table

| Likelihood Indicator | Criteria |
|---|---|
| 4 | None Of A Or B Or C Is True AND Both LASA Drug Pair Members Are Oral Solids |
| 5 | None Of A Or B Or C Is True AND One Or More Decreasing Factors Are Present |

A = Levenshtein Distance Of 5 Or Less
B = High-Low or Low-Low Prescribing Frequencies
C = Presence Of One Or More Same, Look-Alike Or Sound-Alike Strengths Table 3 illustrates that the combination of a Levenshtein Distance of 5 or less, a pair of high-low or low-low prescribing frequencies, and the presence of at least one same, look-alike or sound-alike strengths may be determined to give rise to the highest likelihood of a LASA medication error. Any two of those criteria may also give rise to the highest likelihood of a LASA medication error, if both LASA drug pair members arc of the same dosage form that is not an oral solid. An oral solid dosage form may be considered a likelihood diminishing factor because oral solids are more readily distinguished from each other than are other dosage forms. In addition, other factors that may enhance or diminish the likelihood of a LASA medication error may be identified through statistical analysis of historical prescription claim transactions which involved actual LASA medication errors or false detections thereof.

Accordingly, Likelihood Indicators may be determined for all drug products associated with active LASA drug pairs, based on similarity of the drug names, prescribing frequencies, availability in same, look-alike or sound-alike strengths and other characteristics of the LASA drug pair members. Multiple Likelihood indicators may be determined for a drug product if that drug product is associated with multiple LASA drug pairs. Likelihood Messages generated based on Likelihood Indicators may indicate the LASA alternative drug names with which there is a likelihood of a LASA medication error. Multiple LASA alternative drug names may potentially be included in a Likelihood Message. In certain embodiment, if at least one Likelihood Indicator is equal to a particular value or values (e.g., 1 or 2), every LASA alternative drug name may be inserted into the Likelihood Message and may be ordered according to clinical significance of the associated LASA drug pairs.

The exemplary Likelihood Screening process 220 begins at starting block 501 and progresses to step 502, where all active LASA drug pair associated with the submitted drug product are selected. As mentioned previously, a list or table of LASA drug pairs may be stored in a database 105. A system administrator, such as a pharmacy manager, may specify which of the LASA drug pairs is the be considered "active" and therefore examined during the Likelihood Screening process 220. It is assumed, based on the flow of FIG. 2, that the submitted drug product belongs to at least one active LASA drug pair; if not, the Likelihood Screening process 220 would not be performed. However, those skilled in the art will appreciate that the Likelihood Screening process 220 may be used outside the context of FIG. 2 and could thus be modified to include a database check for at least one active LASA drug pair associated with the submitted drug product.

Next at step 504, the database 105 is queried to determine the Likelihood Indicator(s) for the submitted drug product in relation to each of the selected LASA drug pairs. The method next moves to step 506, where a determination is made as to whether the prescription claim relates to a new prescription. If the prescription claim relates to a new prescription, the method proceeds to step 508 where the Likelihood Message and Likelihood Edit Action are determined for a new prescription, based on the Likelihood Indicators. If the prescription claim does not relate to a new prescription, the method proceeds to step 510 where the Likelihood Message and Likelihood Edit Action are determined for a refill prescription, based on the Likelihood Indicators. To determine applicable Likelihood Messages and Likelihood Edit Actions, a look-up table or other data structure containing such information may be consulted. An exemplary look-up table is illustrated below as Table 4.

TABLE 4

Likelihood Messages and Edit Actions

| Likelihood Indicator | New Rx | Refill Rx | Likelihood Message: |
|---|---|---|---|
| 1 | Edit Action = Reject | Edit Action = Reject | "LASA Drug-[Drug Name of Submitted Drug Product] looks/sounds like [LASA Alternative Drug Name(s)]" |
| 2 | Edit Action = Reject | Edit Action = Capture | "LASA Drug-[Drug Name of Submitted Drug Product] looks/sounds like [LASA Alternative Drug Name(s)]" |
| 3 | Edit Action = Capture | Edit Action = Capture | "LASA Drug-[Drug Name of Submitted Drug Product] looks/sounds like [LASA Alternative Drug Name(s)]" |
| 4 | Edit Action = Capture | Edit Action = None | "LASA Drug-[Drug Name of Submitted Drug Product] looks/sounds like [LASA Alternative Drug Name(s)]" |
| 5 | Edit Action = None | Edit Action = None | "LASA Drug-[Drug Name of Submitted Drug Product] looks/sounds like [LASA Alternative Drug Name(s)]" |

As shown in Table 4, it may be administratively determined that any prescription claim transaction involving a submitted drug product having at least one Likelihood Indicator of I should be rejected, whether the prescription claim relates to a new prescription claim or a refill. Similarly, any prescription claim transaction involving a submitted drug product having at least one Likelihood Indicator of 2 should be rejected if the prescription claim relates to a new prescription claim, but should only be captured (recorded) in the case of a refill. As mentioned previously, Likelihood Edit Action parameters may be modified by a system administrator. Again, in certain embodiment, if any Likelihood Indicator for a submitted drug product corresponds to a Reject Likelihood Edit Action, all LASA alternative drug names may be inserted into the Likelihood Message.

Likelihood Messages may be used to alert a pharmacist that a submitted drug product has a drug name that looks and/or sounds like a LASA alternative drug name, in cases where confusion between the two drug names is likely. In other embodiments, Likelihood Messages may provide other details besides the LASA alternative drug names. For example, Likelihood Messages may indicate whether the drug products associated with the LASA drug pair are newly available, which may serve as extra incentive to the pharmacists to double-check the drug name of the submitted drug product. After determining a Likelihood Message and Likelihood Edit Action for the selected LASA drug pair at either step 508 or step 510, the method ends at step 512.

Figure 6:
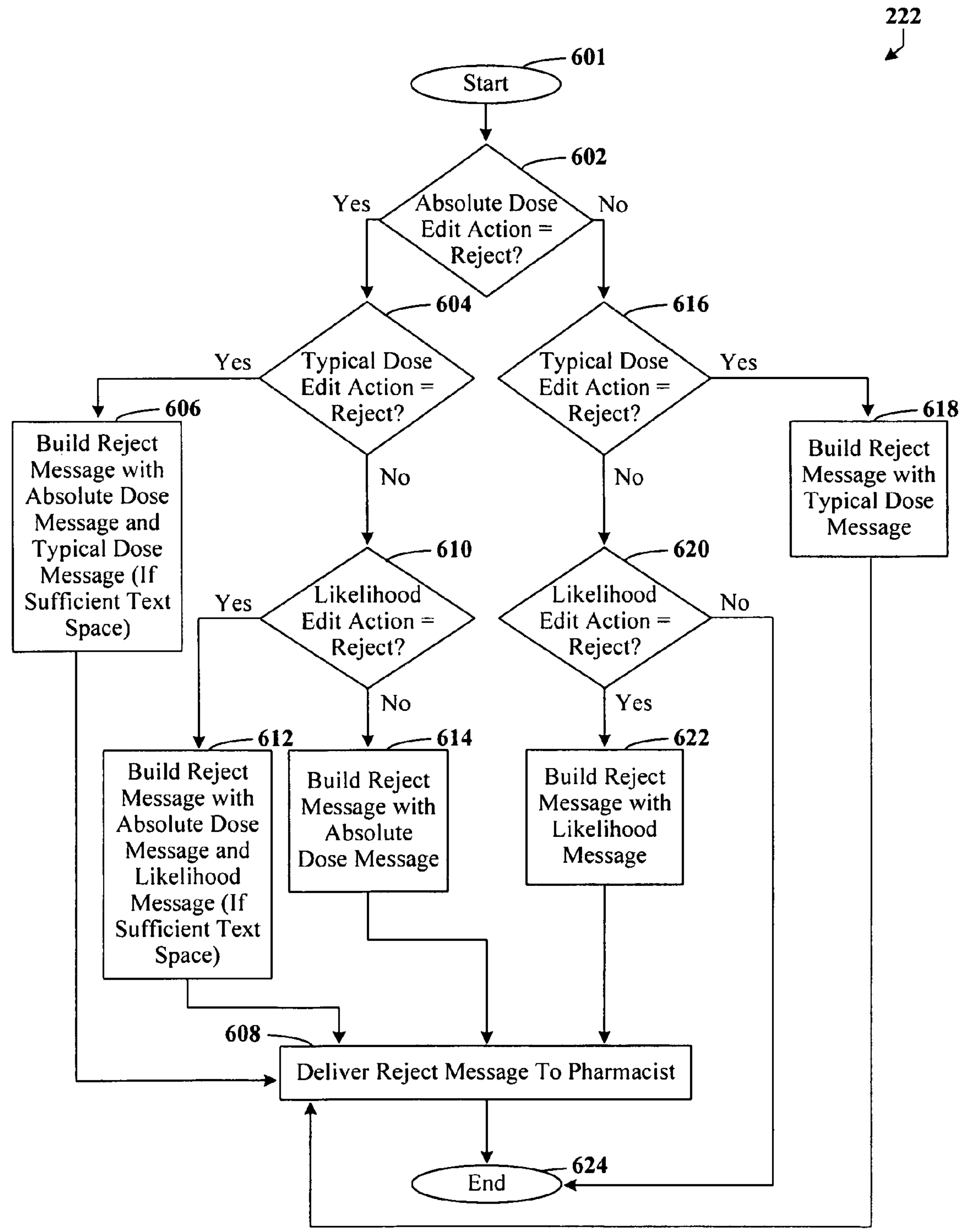
FIG. 6 is a flow chart illustrating an exemplary reject message build and delivery method in accordance with certain exemplary embodiments of the present invention.

FIG. 6 is a flow chart illustrating an exemplary Reject Message build and delivery process 222 (from FIG. 2) in accordance with certain embodiments of the present invention. The method begins at start block 601, where it is assumed that all screening processes have been completed and any Absolute Dose Message and Absolute Dose Edit Action, Typical Dose Messages and Typical Dose Edit Actions and Likelihood Messages and Likelihood Edit Actions have been identified. As previously mentioned, a Reject Message is preferably built only if one or more Reject Edit Actions were identified by the various screening processes. Furthermore, if a Reject Message is built, it may include all screening messages (Absolute Dose Message, Typical Dose Message and/or Likelihood Messages) associated with Reject Edit Actions, or only a subset thereof. The exemplary Reject Message build and delivery process 222 includes only a subset of the screening messages in a Reject Message, so as to avoid including redundant information and to account for text space limitations.

Thus, at step 602 a determination is made as to whether an Absolute Dose Edit Action of Reject was identified by the Absolute Dose Screening process. If so, the method moves to step 604, where a determination is made as to whether a Typical Dose Edit Action of Reject was generated by the Typical Dose Screening process. If a Typical Dose Edit Action of Reject was generated by the Typical Dose Screening process, the method advances to step 606, where a Reject Message is built and populated with the Absolute Dose Message and the Typical Dose Message (if sufficient text space is available). The Reject Message built at step 606 does not include any Likelihood Message(s), even if one or more Likelihood Edit Actions of Reject was identified. After building a Reject Message at step 606, the Reject Message is delivered to the pharmacist (e.g., to the pharmacy POS device 102) at step 608 and the method ends at step 624.

However, if it is determined at step 604 that no Typical Dose Edit Action of Reject was generated by the Typical Dose Screening process, the method advances to step 610 where a determination is made as to whether a Likelihood Edit Action of Reject was generated by the Likelihood Screening process. If it is determined at step 610 that a Likelihood Edit Action of Reject was generated, a Reject Message is built and populated with the Absolute Dose Message and the Likelihood Message(s) (as text space permits) at step 612. If it is determined at step 610 that no Likelihood Edit Action of Reject was generated, a Reject Message is built and populated with only the Absolute Dose Message at step 614. After building a Reject Message at step 612 or step 614, the Reject Message is delivered to the pharmacist at step 608 and the method ends at step 624.

Returning to step 602, if it is determined that no Absolute Dose Edit Action of Reject was identified by the Absolute Dose Screening process, the method moves to step 616, where a determination is made as to whether a Typical Dose Edit Action of Reject was generated by the Typical Dose Screening process. If a Typical Dose Edit Action of Reject was generated by the Typical Dose Screening process, the method advances to step 618, where a Reject Message is built and populated with only the Typical Dose Message. The Reject Message built at step 618 does not include any Likelihood Message(s), even if one or more Likelihood Edit Actions of Reject was identified. After building a Reject Message at step 618, the Reject Message is delivered to the pharmacist (e.g., to the pharmacy POS device 102) at step 608 and the method ends at step 624.

However, if it is determined at step 616 that no Typical Dose Edit Action of Reject was generated by the Typical Dose Screening process, the method advances to step 620 where a determination is made as to whether a Likelihood Edit Action of Reject was generated by the Likelihood Screening process. If it is determined at step 620 that a Likelihood Edit Action of Reject was generated, a Reject Message is built and populated with only the Likelihood Message at step 622. After building a Reject Message at step 622, the Reject Message is delivered to the pharmacist at step 608 and the method ends at step 624. If it is determined at step 620 that no Likelihood Edit Action of Reject was generated, the method ends at step 624 without building a Reject Message.

As may be seen from the foregoing, the present invention provides systems and methods for analyzing prescription claim transactions in order to identify potential LASA medication errors. Any one or more of the above described screening processes, or other screening processes, may be used to identify potential LASA medication errors. If potential LASA medication errors are identified, appropriate Reject Messages may be transmitted to the pharmacist. Potential LASA medication errors may also be recorded for subsequent analysis and reporting.

It should be appreciated that the exemplary aspects and features of the present invention as described above are not intended to be interpreted as required or essential elements of the invention, unless explicitly stated as such. It should also be appreciated that the foregoing description of exemplary embodiments was provided by way of illustration only and that many other modifications, features, embodiments and operating environments are possible. For example, the present invention is not intended to be limited to the prescription claim editing environment. In other embodiments, one or more of the LASA medication error screening processes can be readily adapted for application in electronic prescription systems, hospital inpatient medication ordering systems, etc.

In still other embodiments, a number of enhancements may be provided for improving the sensitivity and specificity of the above-described LASA medication error screening processes. By way of illustration, the Typical Dose Screening process may be modified to include age-tiered typical dosing criteria, physician specialty-specific typical dosing criteria, gender-specific typical dosing criteria, disease-specific typical dosing criteria, and the like.

As another example, the Absolute Dose Screening and Typical Dose Screening processes may be adapted for use in connection with all prescription claim transactions, not just those involving a member of a LASA drug pair. Such an adaptation to the Typical Dose Screening process would allow a pharmacist to be informed, for any drug product, when it is determined that the submitted daily dosage is highly unusual for the patient's age and/or sex, even though it might satisfy absolute maximum and minimum dosing criteria. Such a system could also provide warnings that a particular drug product is never used in a given patient population or that it is highly unusual for a physician of a particular specialty to be prescribing a particular drug product. The Typical Dose Screening process could also be adapted to account for criteria in addition to typical dose criteria, such as typical ingredient(s)/strength(s)/dosage form combinations for patient group and/or typical days supply.

In other embodiments, pharmacists may be provided with context-sensitive messages regarding Continuing Education programs. The context sensitive messages may be included in Reject Messages or in separately delivered transmissions, such as email messages or facsimiles. Based on sponsor-identified triggers, individual pharmacists can be directed to appropriate drug-focused or disease-focused Continuing Education programs and may be informed as to the trigger event that resulted in the invitation. Trigger events could include having a particular drug or drug class exceed a preset threshold in terms of percent of total prescriptions, or number of prescription dispensed in a week or month. A trigger event could also include dispensing the first prescription for a brand new drug. Or, for very rare but complex drugs or diseases, a trigger event may occur every time a related new prescription is dispensed. These and other trigger events will occur to those of ordinary skill in the art.

Therefore, it is contemplated that any and all such embodiments are included in the present invention as may fall within the literal or equivalent scope of the appended claims. The scope of the present invention is to be limited only by the following claims and not by the foregoing description of exemplary and alternative embodiments.

We claim:

1. A method for look-alike sound-alike medication error messaging, comprising:

calculating, by a host server, a set of most common daily dosage (MCDD) values or a set of common daily dosage (CDD) values for each of a plurality of drug products, based at least in part on dosage values from previously received prescription claim transactions received by the host server from a plurality of pharmacy point of service (POS) devices;

storing, in a database accessible by the host server, the MCDD or CDD value sets for each of the plurality of drug products;

receiving, at the host server, a prescription claim transaction from a pharmacy POS device;

determining, from the prescription claim transaction received at the host server, a submitted drug product and a submitted daily dosage for the submitted drug product, wherein the submitted drug product is one of the plurality of drug products stored in the database;

determining, by the host server, that the submitted drug product is associated with at least one look-alike sound-alike alternative drug product;

determining, by the host server, that the submitted daily dosage is not within the MCDD or CDD value sets for the submitted drug product based on a comparison of the submitted daily dosage to the MCDD or CDD value sets for the submitted drug product;

determining, by the host server, that the submitted daily dosage is within the MCDD or CDD value sets for the at least one look-alike sound-alike alternative drug product based on a comparison of the submitted daily dosage to the MCDD or CDD value sets for the at least one look-alike sound-alike alternative drug product;

determining that the prescription claim transaction should be rejected based at least in part on the determination that the submitted daily dosage is within the MCDD or CDD value sets for the at least one look-alike sound-alike alternative drug product;

generating a reject message at the host server, wherein the reject message indicates a potential prescription error has been detected; and transmitting the reject message from the host server to the pharmacy POS device.

2. The method of claim 1, wherein determining that the prescription claim transaction should be rejected includes determining a likelihood indicator, wherein the likelihood indicator represents a relative probability of whether the submitted drug product is involved in a look-alike sound-alike medication error involving the at least one look-alike sound-alike alternative drug product.

3. The method of claim 2, wherein the likelihood indicator is determined based on a degree of similarity between drug names of the submitted drug product and the at least one look-alike sound-alike alternative drug product, prescribing frequencies of the submitted drug product and the at least one look-alike sound-alike alternative drug product, and whether the submitted drug product and the at least one look-alike sound-alike alternative drug product are available in similar strengths.

4. The method of claim 3, wherein the prescribing frequencies of the submitted drug product and the at least one look-alike sound-alike alternative drug product are categorized as being either high, medium or low; and wherein a low-low, high-low or low-high combination of prescribing frequencies is considered to have the potential for confirmation bias.

5. The method of claim 1, wherein determining that the prescription claim transaction should be rejected includes determining whether the submitted daily dosage meets absolute dosing criteria for the submitted drug product.

6. The method of claim 5, wherein the absolute dosing criteria is specific to at least one of the group consisting of: patient demographic group, treatment type and illness type.

7. The method of claim 5, wherein the submitted daily dosage is determined to not meet the absolute dosing criteria for the submitted drug product because the submitted daily dosage is lower than an absolute minimum daily dosage for the submitted drug product.

8. The method of claim 5, wherein the submitted daily dosage is determined to not meet the absolute dosing criteria for the submitted drug product because the submitted daily dosage exceeds an absolute maximum daily dosage for the submitted drug product.

9. The method of claim 1, wherein the CDD value set for each of a plurality of drug products is within a daily dosage range above a predefined percentage of all dosage values of the previously received prescription claim transactions associated with the submitted drug product.

10. The method of claim 9, wherein the MCDD value set for a particular drug product is within a daily dosage range above a predefined percentage of all dosage values of the previously received prescription claim transactions associated with the submitted drug product, the percentage being larger and the range being narrower than that used to determine the CDD value set for that particular drug product.

11. The method of claim 1, wherein determining that the submitted daily dosage is not within the MCDD or CDD value sets for the submitted drug product includes determining that the submitted daily dosage is not within a deviation of at least one value of the MCDD or CDD value sets.

12. The method of claim 11, wherein each of the MCDD or CDD value sets includes one or more values.

13. The method of claim 1, wherein determining that the prescription claim transaction should be rejected includes determining whether the prescription relates to the new prescription or a refill.

14. The method of claim 1, wherein determining that the prescription claim transaction should be rejected includes determining a clinical significance for the look-alike sound-alike drug pair, the clinical significance being a value used to quantify the consequences of a look-alike sound-alike medication error involving the look-alike sound-alike drug pair.

15. The method of claim 1, wherein each of the MCDD or CDD value sets is specific to at least one of the group consisting of: patient demographic group, treatment type, illness type and physician specialty.

16. The method of claim 1, wherein the reject message identifies the at least one look-alike sound-alike alternative drug product.

17. A system for look-alike sound-alike medication error messaging, comprising:

a network interface;

a database; and a processor, located at a host server, in communication with the network interface and the database, wherein the processor is configured to:

calculate a set of most common daily dosage (MCDD) values or a set of common daily dosage (CDD) values for each of a plurality of drug products, based at least in part on dosage values from previously received prescription claim transactions received by the host server from a plurality of pharmacy point of service (POS) devices;

store, in the database, the MCDD or CDD value sets for each of the plurality of drug products;

receive, via the network interface, a prescription claim transaction from a pharmacy point of service (POS) device;

determine, from the prescription claim transaction, a submitted drug product and a submitted daily dosage for the submitted drug product, wherein the submitted drug product is one of the plurality of drug products stored in the database;

determine that the submitted drug product is associated with at least one look-alike sound-alike alternative drug product;

determine that the submitted daily dosage is not within the MCDD or CDD value sets for the submitted drug product based on a comparison of the submitted daily dosage to the MCDD or CDD value sets for the submitted drug product;

determine that the submitted daily dosage is within the MCDD or CDD value sets for the at least one look-alike sound-alike alternative drug product based on a comparison of the submitted daily dosage to the MCDD or CDD value sets for the at least one look-alike sound-alike alternative drug product;

determine that the prescription claim transaction should be rejected based at least in part on the determination that the submitted daily dosage is within the MCDD or CDD value sets for the at least one look-alike sound-alike alternative drug product;

generate a reject message, wherein the reject message indicates a potential prescription error has been detected; and transmit the reject message from the host server to the pharmacy POS device.

18. The system of claim 17, wherein the computer-executable instructions to determine that the prescription claim transaction should be rejected include computer-executable instructions to determine a likelihood indicator, wherein the likelihood indicator represents a relative probability of whether the submitted drug product is involved in a look-alike sound-alike medication error involving the at least one look-alike sound-alike alternative drug product.

19. The system of claim 18, wherein the likelihood indicator is determined based on a degree of similarity between drug names of the submitted drug product and the at least one look-alike sound-alike alternative drug product, prescribing frequencies of the submitted drug product and the at least one look-alike sound-alike alternative drug product, and whether the submitted drug product and the at least one look-alike sound-alike alternative drug product are available in similar strengths.

20. The system of claim 19, wherein the prescribing frequencies of the submitted drug product and the at least one look-alike sound-alike alternative drug product are categorized as being either high, medium or low; and wherein a low-low, high-low or low-high combination of prescribing frequencies is considered to have the potential for confirmation bias.

21. The system of claim 17, wherein the computer-executable instructions to determine that the prescription claim transaction should be rejected include computer-executable instructions to determine whether the submitted daily dosage meets absolute dosing criteria for the submitted drug product.

22. The system of claim 21, wherein the absolute dosing criteria are specific to at least one of the group consisting of: patient demographic group, treatment type and illness type.

23. The system of claim 21, wherein the submitted daily dosage is determined to not meet the absolute dosing criteria for the submitted drug product because the submitted daily dosage is lower than an absolute minimum daily dosage for the submitted drug product.

24. The system of claim 21, wherein the submitted daily dosage is determined to not meet the absolute dosing criteria for the submitted drug product because the submitted daily dosage exceeds an absolute maximum daily dosage for the submitted drug product.

25. The system of claim 17, wherein the CDD value set for each of a plurality of drug products is within a daily dosage range above a predefined percentage of all dosage values of the previously received prescription claim transactions associated with the submitted drug product.

26. The system of claim 25, wherein the MCDD value set for a particular drug product is within a daily dosage range above a predefined percentage of all dosage values of the previously received prescription claim transactions associated with the submitted drug product, the percentage being larger and the range being narrower than that used to determine the CDD value set for that particular drug product.

27. The system of claim 17, wherein determining that the submitted daily dosage is within the MCDD or CDD value sets for the at least one look-alike sound-alike alternative drug product includes determining that the submitted daily dosage is within a deviation of at least one value of the MCDD or CDD value sets.

28. The system of claim 27, wherein each of the MCDD or CDD value sets includes one or more values.

29. The system of claim 17, wherein the computer-executable instructions to determine that the prescription claim transaction should be rejected include computer-executable instructions to determine whether the prescription relates to the new prescription or a refill.

30. The system of claim 17, wherein the computer-executable instructions to determine that the prescription claim transaction should be rejected include computer-executable instructions to determine a clinical significance for the look-alike sound-alike drug pair, the clinical significance being a value used to quantify the consequences of a look-alike sound-alike medication error involving the look-alike sound-alike drug pair.

31. The system of claim 17, wherein each of the MCDD or CDD value sets is specific to at least one of the group consisting of: patient demographic group, treatment type, illness type and physician specialty.

32. The system of claim 17, wherein the reject message identifies the at least one look-alike sound-alike alternative drug product.

* * * * *